(12) United States Patent
Marx (10) Patent No.: US 11,747,337 B2
(45) Date of Patent: *Sep. 5, 2023

(54) KIT FOR MONITORING, DETECTING AND STAGING GVHD

(71) Applicant: Stephen G. Marx, Jerusalem (IL)

(72) Inventor: Stephen G. Marx, Jerusalem (IL)

( * ) Notice: Subject to any disclaimer, the term of this patent is extended or adjusted under 35 U.S.C. 154(b) by 385 days.

This patent is subject to a terminal disclaimer.

(21) Appl. No.: 16/694,379

(22) Filed: Nov. 25, 2019

(65) Prior Publication Data

US 2020/0088730 A1    Mar. 19, 2020

Related U.S. Application Data

(63) Continuation of application No. 15/276,819, filed on Sep. 27, 2016, now abandoned, which is a continuation-in-part of application No. 13/821,311, filed as application No. PCT/IL2011/000711 on Sep. 7, 2011, now abandoned.

(60) Provisional application No. 61/433,540, filed on Jan. 18, 2011, provisional application No. 61/380,337, filed on Sep. 7, 2010.

(51) Int. Cl.
| | |
|---|---|
| *A61K 39/395* | (2006.01) |
| *A61K 39/44* | (2006.01) |
| *G01N 33/573* | (2006.01) |
| *A61K 31/573* | (2006.01) |
| *A61K 38/13* | (2006.01) |
| *G01N 33/68* | (2006.01) |
| *A61K 45/06* | (2006.01) |

(52) U.S. Cl.
CPC ......... *G01N 33/573* (2013.01); *A61K 31/573* (2013.01); *A61K 38/13* (2013.01); *A61K 39/3955* (2013.01); *A61K 39/39541* (2013.01); *A61K 45/06* (2013.01); *G01N 33/6893* (2013.01); *G01N 2333/91205* (2013.01); *G01N 2440/14* (2013.01); *G01N 2800/245* (2013.01)

(58) Field of Classification Search
CPC ................ A61K 38/13; A61K 2300/00; A61K 39/39541; A61K 31/573; A61K 45/06; A61K 39/3955; G01N 2440/14; G01N 2800/245; G01N 33/6893; G01N 33/573; G01N 2333/91205
See application file for complete search history.

(56) References Cited

U.S. PATENT DOCUMENTS

| | | |
|---|---|---|
| 2003/0228618 A1 | 12/2003 | Levanon et al. |
| 2004/0101907 A1 | 5/2004 | Bussiere et al. |
| 2005/0250178 A1 | 11/2005 | Andrew et al. |
| 2009/0104628 A1 | 4/2009 | Reagan et al. |

FOREIGN PATENT DOCUMENTS

| | | |
|---|---|---|
| WO | 2006006939 A1 | 1/2006 |
| WO | 2008124428 A1 | 10/2008 |
| WO | 2012032511 A2 | 3/2012 |

OTHER PUBLICATIONS

Orbach A. et al.—"Utilizing Glycogen Synthase Kinase-3b as a Marker for the Diagnosis of Graft-versus-Host Disease", Transplantation Proceedings, 2013, vol. 45, pp. 2051-2055. (Year: 2013).*
Huang, "Glycogen synthase kinase-3 negatively regulates anti-inflammatory interleukin-10 for lipopolysaccharide-induced iNOS/NO biosynthesis and RANTES production in microglial cells", Immunology, 2009, pp. e275-286, vol. 128, Supplemental 1.
Iwasaki et al., "Recent Advances in the Treatment of Graft-Versus-Host Disease", Clinical Medicine & Research, 2004, pp. 243-252, vol. 2, No. 4.
Klamer et al., "GSK3 inhibition prevents lethal GVHD in mice", Experimental Hematology, 2013, pp. 39-55, vol. 41, No. 1.
International Search Report of PCT/IL2011/000711, dated May 2, 2012.
Written Opinion of the International Searching Authority of PCT/IL2011/000711, dated May 2, 2012.
International Preliminary Report on Patentability Chapter II of PCT/IL2011/000711, dated Nov. 6, 2012.

* cited by examiner

*Primary Examiner* — Satyendra K Singh
(74) *Attorney, Agent, or Firm* — THE WEBB LAW FIRM (57) ABSTRACT

Provided herein is a method and kit for diagnosing and treating Graft versus host disease (GVHD), the method including obtaining a body fluid or tissue sample from said mammal, throughout the year post-transplant; detecting the expression level, phosphorylation level, or a combination thereof, of biomarkers in said body fluid or tissue sample; diagnosing said mammal with Graft versus host disease (GVHD) when the expression level, phosphorylation level, or a combination thereof of said biomarkers in said body fluid or tissue sample are detected with a deviation of at least about 25% from standard measurements taken from healthy subjects and/or from measurements taken from said mammal prior to said transplant; and, administering an effective amount of at least one immunosuppressant or steroid or a combination thereof to the diagnosed mammal.

5 Claims, 6 Drawing Sheets

KIT FOR MONITORING, DETECTING AND STAGING GVHD

CROSS-REFERENCE TO RELATED APPLICATIONS

The present application is a continuation of U.S. patent application Ser. No. 15/276,819, filed Sep. 27, 2016, which is a continuation-in-part of U.S. patent application Ser. No. 13/821,311, filed Mar. 7, 2013, which is the U.S. National Stage of International Patent Application No. PCT/IL2011/000711, filed Sep. 7, 2011, which claims the benefit of U.S. Provisional Patent Application Nos. 61/433,540 and 61/380,337, filed Jan. 18, 2011 and Sep. 7, 2010, respectively, the disclosures of which are incorporated herein by reference in their entirety.

BACKGROUND OF THE INVENTION

Field of the Invention

The present invention is in the field of diagnostic and regulatory kits for the treatment of conditions associated with pathological cell proliferation. More specifically, the invention is adapted to measure, monitor, and regulate the activation and inactivation levels of glycogen synthase kinase 3 (GSK-3) as a marker of T-cell proliferation, especially in conditions such as Graft versus Host Disease (GVHD).

Background Art

Glycogen synthase kinase 3 (GSK-3) is a serine/threonine kinase that is known to act as a downstream regulatory switch that determines the output of numerous signaling pathways initiated by diverse stimuli. Through these pathways GSK-3 plays a central role in cellular proliferation and apoptosis. The ability to detect the activation state of the GSK-3 and if necessary to regulate it, would allow a greater understanding and ability to treat and diagnose conditions related to cell proliferation and apoptosis.

In many conditions related to the immune response, including tissue rejection, inflammation, infection and GVHD, there is a marked change in cell proliferation, in particular an increase in T-cell proliferation.

The incidence of GVHD has increased substantially over recent years. The number of allogeneic hematopoietic stem cell transplants (HSCT) that occur annually continues to increase each year. GVHD may also occur occasionally as a complication of blood transfusion. Clinically, the diagnosis of GVHD is suspected when the patient develops one or more of the following observable symptoms: dermatitis (skin rash), cutaneous blisters, crampy abdominal pain with or without diarrhea, persistent nausea and vomiting, hepatitis (with elevation of bilirubin and/or liver enzymes) (Jacobsohn D A and Vogelsang G B 2007). Clinical observations along with current diagnostic techniques are time-consuming and require invasive tissue sampling, involving tissue biopsies obtained from an involved organ in order to confirm and diagnose GVHD. Although biopsies are the only way to properly diagnose GVDH today, the diagnosis is determined only after T cells are already attacking the host tissues and the GVHD process has reached phase 3 of the disorder. Biopsy procedures to procure tissue are also invasive and incur delays of 24 to 48 hours before a diagnosis can be rendered. Furthermore, an unequivocal diagnosis is not always possible with biopsies, and diagnosis from clinical symptoms is not reliable, given that other post-transplant conditions may present in a similar manner.

There is therefore a long-felt need to provide a rapid, reliable relatively non-invasive method for detecting GVHD and other pathological conditions involving cell proliferation in the early stages of the disease process.

SUMMARY OF THE INVENTION

The present invention relates to the field of diagnostic and regulatory kits and more specifically to a diagnostic and regulatory kit for Graft versus Host Disease.

It is one object of the present invention to disclose a method of detecting GVHD in a mammal including a human comprising the steps of; obtaining a sample from the patient or subject; and, measuring the level of GSK-3β; wherein a significant deviation from normal values indicates the presence of GVHD.

It is yet another object of the present invention to disclose a method of diagnosing and treating Graft versus host disease (GVHD) in a mammal including a human undergoing transplant, said method comprising: (a) obtaining a body fluid or tissue sample from said mammal, throughout the year post-transplant; (b) detecting the expression level, phosphorylation level, or a combination thereof, of biomarkers selected from the group consisting of: total glycogen synthase kinase-3β(GSK-3β), serine 9 phosphorylated GSK-3β (p-GSK-3β ser 9), proteins associated with the regulation of GSK-3β, and any combination thereof in said body fluid or tissue sample; (c) diagnosing said mammal with Graft versus host disease (GVHD) when the expression level, phosphorylation level, or a combination thereof of said biomarkers in said body fluid or tissue sample are detected with a deviation of at least about 25% from standard measurements taken from healthy subjects and/or from measurements taken from said mammal prior to said transplant; and (d) administering an effective amount of at least one immunosuppressant or steroid or a combination thereof to the diagnosed mammal.

It is yet another object of the present invention to disclose the method as defined in any of the above, wherein said detection is done by protein analysis.

It is yet another object of the present invention to disclose the method as defined in any of the above, wherein an array of antibodies is used for said detection.

It is yet another object of the present invention to disclose the method as defined in any of the above, wherein said array of antibodies are bound to a glass slide or equivalent substrate, or a chip thereby providing a protein chip analysis tool.

It is yet another object of the present invention to disclose the method as defined in any of the above, wherein said biomarkers are selected from the group consisting of Total GSK-3β, ser 9 phosphorylated GSK-3β, GSK-3β ser 9 phosphorylation PKC Activation, b-catenin, Dvl, Akt, Erk, P38 MAPK, GSK-3β Tyrosine 216 Phosphorylation, Serum Albumin, Fas, Bcl family, Cyctochrome C, caspases, Nf-kB, CD25, Cyclin D1, PCNA and p27, phosphorylation sites on GSK-3β and any combination thereof.

It is yet another object of the present invention to disclose the method as defined in any of the above, wherein said detection is done using a diagnostic kit having a protein chip analysis tool or any other protein analysis analytical tool.

It is yet another object of the present invention to disclose the method as defined in any of the above, further comprising at least one of the following steps:

measuring at least one parameter selected from a group consisting of GSK-3β expression levels and phosphorylation levels, GSK-3β activation levels, GSK-3β inactivation levels, serine 9 phosphorylated GSK-3β expression, expression levels and phosphorylation levels of proteins associated with regulating the activation status and function of GSK-3β, phosphorylation sites on the GSK-3β and p-PKC expression;

measuring at least one activation indicator selected from the group consisting of over-expression of GSK-3β, tyrosine 216 phosphorylation and any combination thereof;

determining the expression, phosphorylation and/or inactivation state of GSK-3β by measuring at least one inactivation indicator selected from the group consisting of serine 9 phosphorylation, Wnt activation as determined by β-catenin levels or through a protein marker specific for inactivation of the GSK-3β through the activated Wnt pathway or through the site on the GSK-3β that the activated Wnt pathway affects to stimulate inactivation of the GSK-3β; PKC expression levels or through a protein marker specific for inactivation of the GSK-3β through activated PKC, and any combination thereof; and measuring expression, phosphorylation and/or activation of GSK-3β by measuring at least one activation indicator selected from the group consisting of over-expression of GSK-3β, tyrosine 216 phosphorylation and any combination thereof.

It is yet another object of the present invention to disclose the method as defined in any of the above, comprising additional steps of measuring the levels of changes in expression levels and phosphorylation levels for pathways and proteins associated with regulating the activation status and function of GSK-3β, phosphorylation sites on the GSK-3β, apoptosis markers, proliferation markers, and other biological and biochemical molecules.

It is yet another object of the present invention to disclose the method as defined in any of the above, comprising additional steps of: (a) measuring the level of GSK-3β inactivation in said sample by at least one assay selected from the group consisting of measuring β-catenin levels in the absence of serine 9 phosphorylation, measuring stimulation levels at the site on the GSK-3β stimulated through the activated Wnt pathway, measuring a protein marker that is unique to the inactivation of the GSK-3β through the activated Wnt pathway and measuring a protein marker that is unique to the inactivation of the GSK-3β through the activated PKC; and (b) comparing the result of said inactivation levels with a predetermined normal inactivation value obtained from healthy subjects and time 0 from said patient, wherein an increased deviation of at least about 25% from normal inactivation values indicates the presence of GVHD.

It is yet another object of the present invention to disclose the method as defined in any of the above, comprising at least one additional step selected from the group consisting of;

measuring GSK-3β inactivation indicators;
measuring GSK-3β activation indicators;
combining measurements of activation and inactivation indicators;
measuring changes in expression levels and phosphorylation levels for pathways and proteins associated with regulating the activation status and function of the GSK-3ββ;
measuring changes in phosphorylation of the phosphorylation sites on the GSK-3ββ;

measuring changes in expression levels or phosphorylation levels for GSK-3β upstream and downstream proteins and pathways and on the GSK3 GSK-3β molecule itself, wherein an activation to inactivation ratio is obtained, characteristic of GVHD.

It is yet another object of the present invention to disclose a method of diagnosing and treating Graft versus host disease (GVHD) in a mammal including a human undergoing transplant, said method comprising: (a) obtaining a body fluid or tissue sample from said mammal, throughout the year post-transplant; (b) detecting the level of biomarkers selected from the group consisting of: total glycogen synthase kinase-3β(GSK-3β), serine 9 phosphorylated GSK-3β (p-GSK-3β ser 9), and any combination thereof in said body fluid or tissue sample; (c) diagnosing said mammal with Graft versus host disease (GVHD) when the level of said biomarkers in said body fluid or tissue sample is detected with a decreased deviation of at least about 25% from standard measurements taken from healthy subjects and/or from measurements taken from said mammal prior to said transplant; and (d) administering an effective amount of at least one immunosuppressant or steroid or a combination thereof to the diagnosed mammal.

It is yet another object of the present invention to disclose the method as defined in any of the above, further comprising steps of measuring GSK-3β expression levels.

It is yet another object of the present invention to disclose the method as defined in any of the above, further comprising steps of measuring GSK-3β activation levels.

It is yet another object of the present invention to disclose the method as defined in any of the above, further comprising steps of measuring GSK-3β inactivation levels.

It is yet another object of the present invention to disclose the method as defined in any of the above, further comprising steps of measuring serine 9 phosphorylated GSK-3β expression.

It is yet another object of the present invention to disclose the method as defined in any of the above, further comprising steps of measuring p-PKC expression.

It is yet another object of the present invention to disclose the method as defined in any of the above, further comprising steps of sampling the spleen.

It is yet another object of the present invention to disclose the method as defined in any of the above, further comprising steps of sampling the blood.

It is yet another object of the present invention to disclose the method as defined in any of the above, further comprising steps of sampling a body fluid or tissue.

It is yet another object of the present invention to disclose the method as defined in any of the above, further comprising steps of comparing the result of said GSK-3β levels with a predetermined normal value obtained from healthy subjects.

It is yet another object of the present invention to disclose the method as defined in any of the above, further comprising steps of comparing the result of said expression levels and/or phosphorylation levels of the proteins and pathways associated with the GSK-3β, with predetermined normal value obtained from healthy subjects.

It is yet another object of the present invention to disclose the method as defined in any of the above, further comprising steps of comparing the result of said expression levels and/or phosphorylation levels of the proteins and pathways associated with the GSK-3β with a predetermined normal value obtained from the transplant patient prior to the transplant and/or monitoring the transplant patient for changes in the expression levels and/or phosphorylation levels of the proteins and pathways associated with the GSK-3β over time, and optionally comparing the result of said expression levels and/or protein levels of the proteins and pathways associated with the GSK-3β with predetermined normal values obtained from healthy subjects.

It is yet another object of the present invention to disclose the method as defined in any of the above, further comprising steps of comparing the result of said GSK-3β levels with a predetermined normal value obtained from healthy subjects, wherein a deviation of at least about 25% from normal inactivation values indicates the presence of GVHD.

It is yet another object of the present invention to disclose the method as defined in any of the above, comprising the steps of; obtaining a sample from the patient or subject, measuring the level of GSK-3β, comparing the result of said levels with a predetermined normal value obtained from healthy subjects, such that a deviation of at least about 25% from normal values indicates the presence of GVHD.

It is yet another object of the present invention to disclose a method of detecting GVHD in a mammal including a human comprising the steps of; obtaining a sample from the patient or subject, measuring the level of GSK-3β inactivation by measuring β-catenin levels in the absence of serine 9 phosphorylation, or by measuring the site of stimulation on the GSK-3β once stimulated through the activated Wnt pathway, or by measuring a protein marker that is unique to the inactivation of GSK-3β through the activated Wnt pathway, comparing the result of said inactivation levels with a predetermined normal inactivation value obtained from healthy subjects, such that a deviation of at least about 25% from normal inactivation values indicates the presence of GVHD.

It is yet another object of the present invention to disclose a method of detecting GVHD in a mammal including a human comprising the steps of; obtaining a sample from the patient or subject; measuring the level of GSK-3β inactivation by measuring a protein marker that is unique to the inactivation of GSK-3β through the activated PKC; comparing the result of said inactivation levels with a predetermined normal inactivation value obtained from healthy subjects, wherein a significant deviation from normal inactivation values indicates the presence of GVHD.

It is yet another object of the present invention to disclose a method of detecting GVHD as defined in any of the above, further comprising steps of sampling the blood.

It is yet another object of the present invention to disclose a method of detecting GVHD as defined in any of the above, further comprising steps of sampling the spleen.

It is one object of the present invention to disclose a diagnostic kit for the identification and diagnosis of a pathological process associated with GVHD, in which the diagnostic molecule is GSK-3β.

It is yet another object of the present invention to disclose a diagnostic kit for the identification and diagnosis of a pathological process associated with GVHD wherein the kit is adapted for detecting the expression level of GSK-3β.

It is yet another object of the present invention to disclose a diagnostic kit for the identification and diagnosis of a pathological process associated with GVHD wherein the kit is adapted to detecting expression of p-PKC.

It is yet another object of the present invention to disclose a diagnostic kit for the identification and diagnosis of a pathological process associated with GVHD, such that the activation status of GSK-3β is a determinant of said pathological process.

It is also in the scope of the present invention to disclose a diagnostic kit for the detection of GVHD such that GVHD is detectable during phase 2 of the disease.

It is also in the scope of the present invention to disclose a diagnostic kit for the detection of GVHD such that the activation and/or expression status of GSK-3β is a marker for the progression and/or presence of GVHD.

It is also in the scope of the present invention to disclose a diagnostic kit for the detection of GVHD wherein the changes in expression levels, phosphorylation levels of GSK-3β, the pathways and proteins associated with the regulation of GSK-3β or a combination thereof, is a marker for the progression and/or presence of GVHD.

In yet another preferred embodiment of the present invention, a diagnostic kit for the detection of GVHD is disclosed, in which the activation and/or expression status of GSK-3β is a marker for the progression and/or presence of GVHD.

In yet another preferred embodiment of the present invention, a diagnostic kit for the detection of GVHD is disclosed, wherein the changes in expression levels, phosphorylation levels or a combination thereof of the pathways and proteins associated with the regulation of GSK-3β and/or changes in the phosphorylation sites on the GSK-3β is a marker for the progression and/or presence of GVHD.

In yet another preferred embodiment of the present invention, a diagnostic kit for the detection of GVHD is disclosed, in which monitoring pathways and proteins upstream of the GSK-3β, all the phosphorylation sites on the GSK-3β and pathways and proteins downstream of the GSK-3β (the substrates of GSK-3β and each of their individual product(s)) is utilized as a marker for the progression and/or presence of GVHD. In yet another preferred embodiment of the present invention, a diagnostic kit for the detection of GVHD is disclosed, in which the activation status and/or expression level of GSK-3β is determined by examining markers for the Wnt pathway or the actual site on the GSK-3β being affected by the activated Wnt pathway.

It is yet another object of the present invention to disclose a diagnostic kit for the detection of GVHD, in which the activation status and/or expression level and/or expression level of GSK-3β is a marker for the progression and/or presence of GVHD, further wherein the activation status of GSK-3β is determined by examining serine 9 phosphorylation markers on the GSK-3β molecule.

In another aspect of the present invention, a diagnostic kit for the detection of GVHD is disclosed, in which the activation status and/or expression level of GSK-3β is a marker for the progression or presence of GVHD, and in which furthermore the activation status and/or expression level of GSK-3β is determined by measuring PKC activation sites on GSK-3β, PKC expression and/or a protein marker specific for activated PKC inactivation of the GSK-3β.

It is also in the scope of the present invention to disclose a diagnostic kit for the detection of GVHD, in which over-activation of GSK-3β is determined by measuring tyrosine 216 phosphorylation.

It is also in the scope of the present invention to disclose a diagnostic kit for the detection of GVHD, in which over-activation of GSK-3β is determined by measuring the expression levels of GSK-3β.

In yet another aspect of the present invention, a diagnostic kit for the detection of GVHD is disclosed, in which the presence of over-inactivated GSK-3β as indicated by abnormal levels of phosphorylated serine 9 provides a positive diagnosis of GVHD.

In yet another preferred embodiment of the present invention, a diagnostic kit for the detection of GVHD is disclosed, provided with the means for detecting the presence of over-inactivated GSK-3β as indicated by abnormal levels of β-catenin in the absence of serine 9 phosphorylation, or as indicated by abnormal levels of stimulation at the site on the GSK-3β affected by the activated Wnt pathway, or as indicated by abnormal levels of a protein marker that is unique to the inactivation of GSK-3β through the activated Wnt pathway thereby providing a positive diagnosis of GVHD.

It is yet another object of the present invention to disclose a diagnostic kit for the detection of GVHD, provided with the means for detecting the presence of over-inactivated GSK-3β as indicated by abnormal levels of stimulation at the site on the GSK-3β affected by activated PKC, or as indicated by abnormal levels of a protein marker that is unique to the inactivation of GSK-3β through activated PKC thereby providing a positive diagnosis of GVHD.

It is yet another object of the present invention to disclose a diagnostic kit for the detection of GVHD, provided with the means for detecting the presence of over-inactivated GSK-3β as indicated by abnormal levels of phosphorylated serine 9; and by abnormal levels of markers for Wnt activity including but not limited to abnormal levels of β-catenin expression, abnormal levels of stimulation at the site on the GSK-3β affected by the activated Wnt pathway, abnormal levels of protein markers unique to the inactivation of GSK-3β through the activated Wnt pathway; or any combination thereof, thereby providing a positive diagnosis of GVHD.

It is yet another object of the present invention to disclose a diagnostic kit for the detection of GVHD, provided with the means for detecting the presence of over-inactivated GSK-3β as indicated by abnormal levels of phosphorylated serine 9; and by abnormal levels of markers for activated PKC inactivation of the GSK-3β including but not limited to abnormal levels of stimulation at the site on the GSK-3β affected by the activated PKC, and abnormal levels of protein markers unique to the inactivation of GSK-3β through activated PKC, or any combination thereof, thereby providing a positive diagnosis of GVHD.

In yet another preferred embodiment of the present invention a diagnostic kit for the detection of GVHD is disclosed, provided with the means for detecting the presence of over-inactivated GSK-3β as indicated by abnormal levels of markers for Wnt activity including but not limited to abnormal levels of β-catenin expression, abnormal levels of stimulation at the site on the GSK-3β affected by the activated Wnt pathway and abnormal levels of protein markers unique to the inactivation of GSK-3β through the activated Wnt pathway; and by abnormal levels of markers for activated PKC inactivation of the GSK-3β including but not limited to abnormal levels of stimulation at the site on the GSK-3β affected by the activated PKC, and abnormal levels of protein markers unique to the inactivation of GSK-3β through activated PKC; or any combination thereof, thereby providing a positive diagnosis of GVHD.

In yet another aspect of the present invention a diagnostic kit for the detection of GVHD is disclosed, provided with the means for detecting the presence of over-inactivated GSK-3β as indicated by abnormal levels of phosphorylated serine 9 and abnormal levels of markers for Wnt activity including but not limited to abnormal levels of β-catenin expression, abnormal levels of stimulation at the site on the GSK-3β affected by the activated Wnt pathway, and abnormal levels of protein markers unique to the inactivation of GSK-3β through the activated Wnt pathway; and by abnormal levels of markers for activated PKC inactivation of the GSK-3β including but not limited to abnormal levels of stimulation at the site on the GSK-3β affected by the activated PKC, and abnormal levels of protein markers unique to the inactivation of GSK-3β through activated PKC; or any combination thereof, thereby providing a positive diagnosis of GVHD.

It is yet another object of the present invention to disclose a diagnostic kit for GVHD, in which the diagnostic kit characterizes the activation status of GSK-3β so as to determine the cause of the GVHD.

It is yet another object of the present invention to disclose a diagnostic kit for GVHD, in which the diagnostic kit characterizes the expression status of GSK-3β so as to determine the cause of the GVHD.

It is yet another object of the present invention to disclose a diagnostic kit for GVHD, wherein the diagnostic kit characterizes the changes in expression levels, phosphorylation levels or a combination thereof of the pathways and proteins associated with the regulation of the GSK-3β and/or changes in the phosphorylation of the phosphorylation sites on the GSK-3β so as to determine the cause of the GVHD.

It is yet another object of the present invention to disclose a diagnostic kit for GVHD, wherein the diagnostic kit monitors pathways and proteins upstream of the GSK-3β, the phosphorylation sites on the GSK-3β and pathways and proteins downstream of the GSK-3β (the substrates of the GSK-3β and each of their individual product(s)) so as to determine the cause of the GVHD.

In yet another preferred embodiment of the present invention, a method of diagnosing GVHD by determining expression and/or inactivation state of GSK-3β is disclosed, by measuring at least one inactivation indicator selected from the group including serine 9 phosphorylation, Wnt activation as determined by β-catenin levels or through a protein marker specific for inactivation of the GSK-3β through the activated Wnt pathway or through the site on the GSK-3β that the activated Wnt pathway affects to stimulate inactivation of the GSK-3β; PKC expression levels, PKC inactivation sites on GSK-3β or through a protein marker specific for inactivation of the GSK-3β through activated PKC, or any combination thereof.

It is another object of the present invention to disclose a method of diagnosing GVHD by measuring expression and/or activation of GSK-3β by measuring at least one activation indicator selected from the group including over-expression of GSK-3β, tyrosine 216 phosphorylation or any combination thereof.

In another preferred embodiment of the present invention, a method of diagnosing GVHD in a mammal including a human is disclosed comprising the steps of; measuring GSK-3β inactivation indicators, measuring GSK-3β activation indicators, combining measurements of activation and inactivation indicators, such that activation to inactivation ratio is obtained characteristic of GVHD.

In yet another aspect of the present invention a diagnostic kit for determining the presence of GVHD by monitoring the activation status and/or expression level of GSK-3β is disclosed in which the diagnostic kit uses further protein markers to further distinguishes between GVHD and other pathological or normal physiological conditions that are also characterized by increased cell proliferation, decreased cell apoptosis and an immune response.

It is another object of the present invention to disclose a diagnostic kit for determining the presence of GVHD, in which an additional positive detection of a unique RNA and/or protein profile for GVHD further verifies the presence of said GVHD during phase 2 of the disease.

In yet another preferred embodiment of the present invention, a diagnostic kit for GVHD is disclosed in which the results provided by said kit indicate the pathways to be modulated to control the activation status of GSK-3β, thereby regulating GVHD.

It is yet another object of the present invention to disclose a diagnostic kit for the detection of the activation status and/or expression levels of GSK-3β, in which the results of the activation status and/or expression level measurement are an indicator for the progression/presence of GVHD.

It is yet another object of the present invention to disclose a diagnostic kit for the detection of changes in expression levels, phosphorylation levels or a combination thereof of the pathways and proteins associated with the regulation of the GSK-3β and the changes in the phosphorylation of the phosphorylation sites on the GSK-3β wherein the changes in the expression levels, phosphorylation levels or a combination thereof of the pathways and proteins associated with the regulation of the GSK-3β and/or the changes in the phosphorylation of the phosphorylation sites on the GSK-3β provide measurements that are an indicator for the progression/presence of GVHD.

It is yet another object of the present invention to disclose a diagnostic kit for the detection of changes in expression levels or phosphorylation levels or a combination thereof of GSK-3β while monitoring proteins and pathways upstream of the GSK-3β, the phosphorylation sites on the GSK-3β and proteins and pathways downstream of the GSK-3β (the substrates of the GSK-3β and each of their individual product(s)) wherein the results of these changes provide measurements which are an indicator for the progression/presence of GVHD.

It is yet another object of the present invention to disclose a diagnostic kit for the detection and quantification of the activation status and/or expression levels of GSK-3β, in which said activation status is an indicator of the cause of GVHD and furthermore in which said activation status and/or expression level is an indicator for the best treatment program.

It is yet another object of the present invention to disclose a diagnostic kit for the detection and quantification of the changes in expression levels, phosphorylation levels or a combination thereof of the pathways and proteins associated with the regulation of the GSK-3β and/or the changes in the phosphorylation of the phosphorylation sites on the GSK-3β wherein said changes are an indicator of the cause of GVHD.

It is yet another object of the present invention to disclose a diagnostic kit for the detection and quantification of the changes in expression levels, phosphorylation levels or a combination thereof of the pathways and proteins associated with the regulation of the GSK-3β and/or the changes in the phosphorylation of the phosphorylation sites on the GSK-3β wherein said changes is an indicator for the best treatment program.

It is yet another object of the present invention to disclose a diagnostic kit for the detection and quantification of changes in expression levels or phosphorylation levels or a combination thereof in monitoring proteins and pathways upstream of the GSK-3β, the phosphorylation sites on the GSK-3β and proteins and pathways downstream of the GSK-3β (the substrates of the GSK-3β and each of their individual product(s)), wherein said changes is an indicator of the cause of GVHD.

It is yet another object of the present invention to disclose a diagnostic kit for the detection and quantification of changes in expression levels or phosphorylation levels or a combination thereof in monitoring proteins and pathways upstream of the GSK-3β, the phosphorylation sites on the GSK-3β and proteins and pathways downstream of the GSK-3β (the substrates of the GSK-3β and each of their individual product(s)), wherein said changes is an indicator for the best treatment program.

It is yet another object of the present invention to disclose a diagnostic kit for the detection of GVHD, in which the GVHD is diagnosed by determining the activation status and/or expression levels of GSK-3β in blood samples from a mammal including a human patient.

It is yet another object of the present invention to disclose a diagnostic kit for the detection of GVHD, wherein the GVHD is diagnosed by determining changes in expression levels, phosphorylation levels or a combination thereof of the pathways and proteins associated with the regulation of the GSK-3β and/or the changes in the phosphorylation of the phosphorylation sites on the GSK-3β in blood samples from a mammal including a human patient.

It is yet another object of the present invention to disclose a diagnostic kit for the detection of GVHD, wherein the GVHD is diagnosed by determining specific changes in expression levels or phosphorylation levels or a combination thereof in monitoring everything upstream of the GSK-3β, all the phosphorylation sites on the GSK-3β and everything downstream of the GSK-3β (All the substrates of the GSK-3β and each of their individual product(s)), in blood samples from a mammal including a human patient.

It is yet another object of the present invention to disclose a protein chip comprising an array of bound antibodies, biomarkers or antigens useful for determining the expression levels, phosphorylation levels or a combination thereof of different GVHD relevant proteins in a given sample.

It is yet another object of the present invention to disclose a protein chip as defined above, comprising antibodies, biomarkers or antigens characteristic of the activation state and/or expression level and/or phosphorylation levels of GSK-3β, the related proteins and pathways associated with the regulation of the GSK-3β (including proteins and pathways upstream, downstream and on the molecule itself), apoptosis markers, proliferation markers, and other biological and biochemical molecules relevant to GVHD wherein said antibodies, biomarkers or antigens are detectable before the appearance of GVHD symptoms in a mammal including a human.

It is yet another object of the present invention to disclose a protein chip as defined above, wherein said antibodies, biomarkers or antigens are selected from the group comprising but not limited to total GSK-3β, ser 9 phosphorylated GSK-3β, GSK-3β ser 9 phosphorylation PKC Activation, b-catenin, Dvl, Akt, Erk, P38 MAPK, GSK-3β Tyrosine 216 Phosphorylation, Serum Albumin, markers for apoptosis comprising Fas, Bcl family, Cyctochrome C and caspases, markers for immune activity comprising Nf-kB and CD25, markers for proliferation comprising Cyclin D1, PCNA and p27), and any combination thereof.

In is yet another preferred embodiment of the present invention to disclose a method of regulating the activation status and/or expression level and/or function of the GSK-3β in a mammal including a human comprising the steps of; obtaining a blood sample from a patient or subject, determining the activation status and/or expression level and/or phosphorylation levels of the proteins and pathways regulating GSK-3β and/or changes in the phosphorylation of the phosphorylation sites on the GSK-3β that are involved in the regulation of the activation state of the GSK-3β and in regulating the function of the GSK-3β, and obtaining a normal activation status and/or expression level and/or phosphorylation level for GSK-3β and its associated pathways and proteins wherein the regulation of said activation status and/or expression level and/or phosphorylation levels of the GSK-3β and its associated pathways and proteins is adapted for controlling GVHD.

It is one object of the present invention to disclose a regulatory and therapeutic kit useful for controlling GVHD, in which the therapeutic molecule is GSK-3β and its associated pathways and proteins.

BRIEF DESCRIPTION OF THE DRAWINGS

The invention is herein described, by way of example only, with reference to the accompanying drawings. The particulars shown are by way of example only and for the purposes of illustrative discussion of the preferred embodiments of the present invention only. The description taken with the drawings should make apparent to those skilled in the art how several forms of the invention may be embodied in practice.

In the drawings.

DETAILED DESCRIPTION OF THE INVENTION

The present invention solves many of the problems of current methods and systems for monitoring patients suffering from conditions associated with pathological cell proliferation and pathological cell apoptosis especially GVHD.

Graft versus Host Disease (GVHD) is a devastating disorder—a serious complication for patients receiving allogeneic hematopoietic stem cell (HSC) transplants. Approximately 35%-50% of transplant patients develop acute GVHD (aGVHD).

Mortality rates for GVHD are high, but depend heavily on the clinical grade of the disease. Clinical grading of GVHD depends on the combined overall involvement of the skin, liver, and intestines; GVHD grades range from I-IV (Glucksburg Scale) through increasing levels of severity. At grades I-II the mortality rate is ~20%, while at grade III mortality rates jump to ~70%, and at grade IV the mortality rate is above 95%. Therefore, early diagnosis and treatment are crucial for disease management. Current diagnostic techniques for GVHD are time-consuming and often highly invasive; diagnostic methods today are based on observation of clinical symptoms and biopsies of affected internal and external organs after symptoms have appeared.

GVHD occurs when T cells from the transplant (graft) attack the tissues of the recipient (host), after perceiving the host tissues as foreign. T-cell proliferation occurs before clinical symptoms appear in the patient. If you do not get an increase in T-cell proliferation GVHD does not occur.

Glycogen Synthase Kinase (GSK-3β) was first found as a serine/threonine kinase that phosphorylates glycogen synthase. It has been shown that GSK-3β acts as a downstream regulatory switch that determines the output of numerous signaling pathways initiated by diverse stimuli. The present invention reveals for the first time that GSK-3β is directly connected to the onset and progression of GVHD. It is shown that GSK-3β plays a central role in regulating T-cell proliferation; inactivation of GSK-3β can stimulate an increase in T-cell proliferation, while activation of GSK-3β can stimulate a decrease in T-cell proliferation.

It is herein shown in an animal model that GSK-3β is directly connected to the onset and progression of GVHD. The present invention demonstrate that through monitoring the activation state of GSK-3β, its substrates and their particular products, GSK-3β can be utilized as a marker for diagnosing the early onset and monitoring the progression of GVHD.

It is therefore a preferred embodiment of the present invention to disclose a diagnostic kit, capable of detecting the expression level, the phosphorylation level and a combination thereof of glycogen synthase kinase 3β (GSK-3β), the pathways and proteins associated with the regulation of the GSK-3β. In this embodiment changes in the expression level, phosphorylation level and/or a combination thereof of the GSK-3β, the pathways and proteins associated with the regulation of the GSK-3β is an indicator of GVHD in the patient.

GSK-3β is now known to act as a downstream regulatory switch that determines the output of numerous signaling pathways initiated by diverse stimuli (Frame and Cohen 2001, Grimes and Jope 2001, Woodgett 2001 and Doble and Woodgett 2003).

The activation status of the GSK-3β, the expression levels or phosphorylation levels of the GSK-3β the pathways and proteins associated with the regulation of the GSK-3β, or the site on the GSK-3β responsible for activating or inactivating of the GSK-3β, are used to detect and monitor GVHD.

Figure 1:
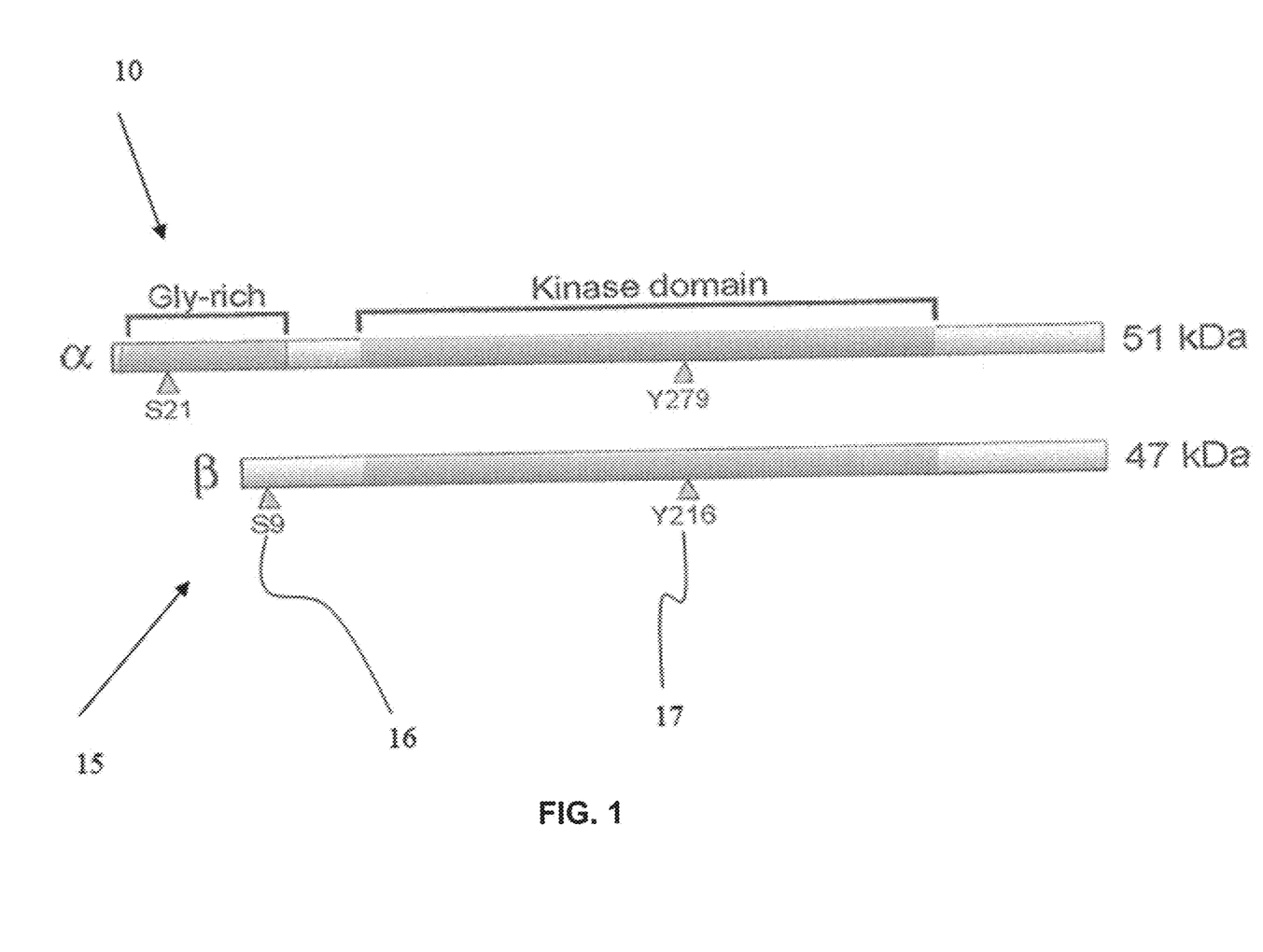
FIG. 1 is a pictorial illustration of the GSK3α and GSK3β subunits and their known activation and inactivation sites.

Reference is now made to FIG. 1 in the drawings, which shows the two subunits of GSK-3, GSK-3α 10 and GSK-3β 15 and their phosphorylation sites. Specific reference is made to the GSK-3β subunit, in which known phosphorylation sites, including the serine 9 (S9) 16 and tyrosine 216 (Y216) 17, are shown. In this embodiment the normal physiological state of the GSK-3β is in an unphosphorylated or dephosphorylated active state. In this embodiment serine 9 phosphorylation inactivates the GSK-3β, which can be identified and quantitated according to the methods described forthwith in the description. Serine 9 phosphorylation is associated with various other proteins including but not limited to cyclic adenosine monophosphate (cAMP), Phosphoinositide 3-kinase (PI3K), Phosphatidylinositol 4,5-biphosphate ($PIP_2$), protein kinase A (PKA) and Akt (serine/threonine protein kinase family).

In a further embodiment of the present invention, GSK-3β inactivation may also occur through the Wnt signaling pathway. Wnt activation inactivates the GSK-3β through an inactivation site independent of serine 9 phosphorylation and is identified and quantitated through measuring changes in non-phosphorylated β-catenin levels.

In a further embodiment activation of the GSK-3β is either through dephosphorylation or through phosphorylation of tyrosine 216 (Y216). GSK-3β phosphorylation can be identified and quantitated through changes in the molecular weight of the GSK-3β using methods described forthwith in the description. In one aspect of this embodiment the diagnostic kit of the present invention uses antibodies to identify and quantify GSK-3β expression levels and phosphorylation levels.

It is a preferred embodiment of the present invention that GSK-3β is a diagnostic and/or therapeutic molecule incorporated into a diagnostic and/or therapeutic kit for detection and monitoring of GVHD.

It is a preferred embodiment of the diagnostic kit of the present invention to characterize GSK3β activity by detecting and quantifying the protein levels of total GSK3β and GSK3β phosphorylated at ser 9. Also in this embodiment, the diagnostic kit is able to detect and quantify GSK3β inactivation through activated protein kinase C (PKC) protein level and GSK3β inactivation through activated Wnt.

Thus it is a preferred embodiment of the present invention to identify GSK-3β associated molecular markers, for example proteins that are affected by the activated Wnt pathway or stimulated by activated PKC to increase the accuracy of GVHD detection, including the site on the GSK-3β that is affected by the activated Wnt pathway and the site on the GSK-3β that is stimulated by activated PKC.

Figure 2:
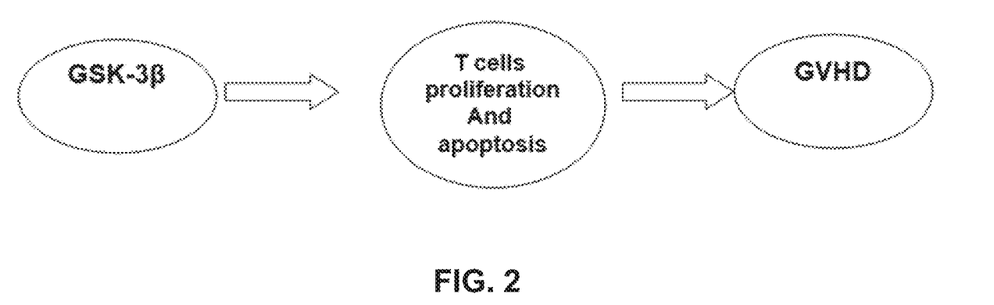
FIG. 2 is a flow diagram connecting GSK3β to GVHD.

Abnormal cell proliferation and apoptosis is a main feature of Graft versus host disease (GVHD) and other conditions related to immune responses in which there is proliferation of T-cells as part of the patient's response to a foreign body or bodies as shown in FIG. 2 of the drawings. In this embodiment and other preferred embodiments the diagnostic molecule and kit is used and has applications in GVHD.

It is a further embodiment of the present invention that regulation of GSK-3β activation status and its associated pathways and proteins by identification and quantification of the expression levels and phosphorylation levels, and inactivation and activation status is adapted to regulate and monitor GVHD. In this embodiment GSK-3β and its associated pathways and proteins, the expression level and phosphorylation level is detected and quantified by the diagnostic kit of the present invention.

A diagnostic kit capable of identifying GVHD in at least phase 2 of the disease by identifying and quantifying the GSK-3β and its associated pathways and proteins through changes in expression levels, phosphorylation levels and activation status, is a further embodiment of the present invention. In this embodiment, the diagnostic kit measures a range of parameters associated with GSK-3β activation states and associated pathways, and compares the deviation from standard measurements taken from healthy subjects in order to determine the extent of GVHD progress and make the appropriate diagnosis of GVHD.

The diagnostic kit of the present invention is adapted to detect the early onset of GVHD by examining changes in the GSK-3β activity by measuring or determining the expression levels, the phosphorylation levels or a combination thereof of GSK-3β and the pathways and proteins associated with the regulation of the GSK-3β and the regulation of the known and established functions of the GSK-3β. Furthermore in this embodiment the diagnostic kit and methods of the present invention will be able to determine the cause of the GVHD with regard to T cell proliferation and apoptosis by determining how the GSK-3β regulates the aforementioned proliferation and apoptosis. In this aspect of the preferred embodiment the information provided by the diagnostic kit is used for determining the most effective treatment for the GVHD through regulating activation and/or inactivation status of the GSK-3β.

It is a further preferred embodiment of the present invention that the diagnostic kit is adapted to detect protein profiles specific and uniquely characteristic to GVHD so as to be able to make a correct and accurate diagnosis of GVHD. In this embodiment the unique protein profile prevents the diagnosis of false positive GVHD.

It is therefore a preferred embodiment of the present invention that the GSK-3β, the pathways and proteins associated with the regulation of the GSK-3β and the regulation of the known and established functions of the GSK-3β acts as a regulatory and therapeutic molecule in a therapeutic or pharmaceutical kit in applications including but not limited to GVHD and tissue rejection.

Figure 3:
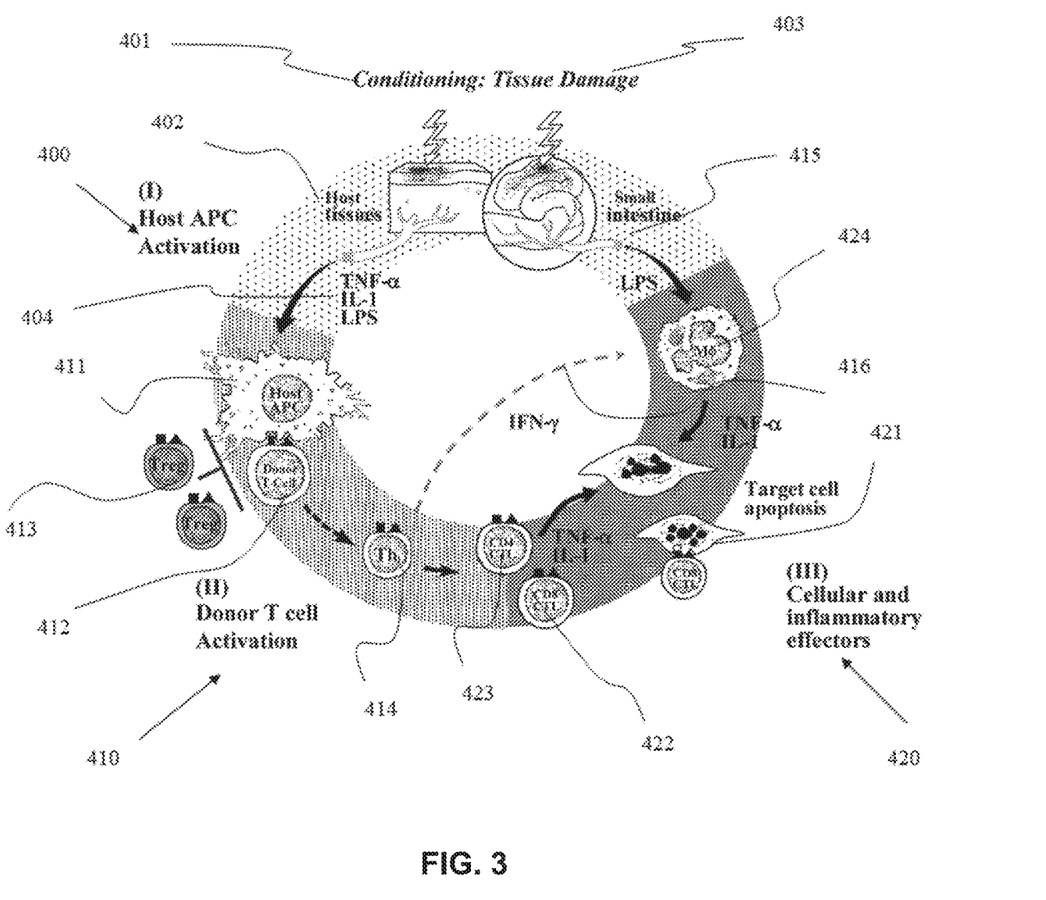
FIG. 3 is a pictorial illustration of the disease process in GVHD.

Reference is now made to FIG. 3 in the drawings in which 3 phases of GVHD disease progression are shown. In phase I 400, antigen presenting cells (APC) are activated, in the process of the recipient conditioning regimen 401, host tissue 402 is damaged 403, causing the release of inflammatory cytokines 404 such as Tumor Necrosis Factor α (TNF-α), Interleukin-1 (IL-1), Interleukin-6 (IL-6) and Lipopolysaccharide (LPS) immune complexes. Increased levels of these cytokines leads to activation of the host APC's. In phase II of GVHD 410 donor T-cell activation and phosphorylation occurs, the host APC's 411 activate donor T-cells 412, this may be prevented by regulatory T cells (Treg) 413. The subsequent increased survival (i.e. decreased apoptosis), proliferation, migration 416 and differentiation of the activated T-cells in phase II of GVHD produces additional effectors that mediate further tissue damage including cytotoxic T Lymphocytes, Natural Killer (NK) cells, TNFα and IL-1. LPS that has leaked through the damaged intestinal mucosa 415 triggers additional TNFα production. TNFα can damage tissue directly by inducing necrosis and apoptosis in the skin and gastrointestinal tract through either TNF receptors or the Fas pathway. TNFα plays a direct role in intestinal GVHD damage which further amplifies damage in the skin, liver and lung in a "cytokine storm". In addition type 1 T helper cells (Th1) 414 are also released in phase II to facilitate the immune response by releasing cytokines and helping in presenting antigens to the T-cells. In phase III of GVHD 420, T-cells target the host tissue for destruction with a range of cellular and inflammatory effectors. Target cells 421 undergo apoptosis and CD4 423, CD8 422 and CTL expressing T-cells are present in the immune response. Macrophages 424 are mediated by LPS and interferon-γ (IFN-γ) in phase 3 of the GVHD disease process. Once activated the macrophages initiate a cascade of inflammatory responses, including the release of mediators of tissue injury—effecting in particular tissues and organs that undergo constant proliferation—such as the gastrointestinal tract and the skin.

It is an embodiment of the present invention that a diagnostic kit capable of detecting and quantitating the expression, the phosphorylation and activation status of the GSK-3β (GSK-3β activation levels and GSK-3β inactivation levels), the pathways and proteins associated with the regulation of the GSK-3β is able to diagnose GVHD during phase II of the disease, at the stage when T-cell proliferation and migration occur. The novel diagnostic kit is able to diagnose GVHD at a relatively early stage before extensive tissue damage occurs, in a quick and relatively non-invasive manner.

In a further embodiment of the present invention, the diagnostic kit for GVHD is able to determine the status of GSK-3β as measured by examining GSK-3β expression levels and phosphorylation levels. The diagnostic kit of the present invention is adapted to accurate and differential diagnosis of GVHD by further detection of unique RNA or protein profiles for GVHD, so as to prevent misdiagnosis with other conditions involving T-cell proliferation and activation.

In another embodiment of the invention, a protein chip utilizing an array of antibodies, biomarkers or antigens bound to a glass slide or equivalent substrate is used to determine the expression levels of different GVHD relevant proteins in a given sample.

In another embodiment of the invention, a diagnostic kit based on a protein chip is used to diagnose GVHD before the appearance of clinical symptoms. In certain embodiments the kit contains a custom-made protein chip comprising antibodies which are adapted to monitor the activation state, the expression level and phosphorylation level of the GSK-3β, the pathways and proteins associated with the regulation of the GSK-3β and the regulation of the known and established functions of the GSK-3β, apoptosis markers, proliferation markers, and other biological and biochemical molecules. Such molecule candidates can be pre-determined and analyzed by western blot, FACS, and other protein analytical and fingerprinting techniques.

In other embodiments of the invention, the establishment of the GVHD diagnostic kit and its efficacy may be tested by the following stages:

GVHD mouse model—samples from mice are utilized to determine the array of antibodies that is loaded on the protein chip or used for any other conventional protein analytical technique. The aforementioned chip is then tested on mouse samples.

Clinical trials—used to determine the efficacy of the protein chip (diagnostic kit prototype) and to predict the development of GVHD in human transplant patients.

In order to understand the invention and to see how it may be implemented in practice, a plurality of preferred embodiments will now be described, by way of non-limiting example only, with reference to the following examples.

Reference is now made to experiments made in a mouse model to determine the involvement of GSK-3β and other proteins from related pathways in GVHD and their potential use as markers for GVHD diagnosis at an early disease stage.

Goal:

To demonstrate that the levels of GSK-3β and proteins from related pathways can be used as markers for GVHD diagnosis at an early disease stage.

GVHD Experimental Mouse Model:

Samples were collected from blood and spleen on days 0, 1, 3, 4, 5, & 6 post-transplant, from the following 3 groups (at least 3 mice per group):

Untreated: injected with of plain medium (no irradiation). Expected result: healthy mice.

Syngeneic: Balb/c mice injected with a splenocyte transplant from matched donor Balb/c mice after irradiation. Expected result: short-term effects of irradiation and full recovery, no GVHD.

Allogeneic: Balb/c mice injected with a splenocyte transplant from unmatched donor C57Bl/6 mice after irradiation. Expected result: short term effects of irradiation and subsequent GVHD development.

Summary of Results:

The levels of p-GSK-3β (ser-9 phosphorylated GSK-3β) and total GSK-3β are much lower in GVHD mice than in both syngeneic and untreated control mice.

The abovementioned effect is seen over time in day's 3-6 post transplant.

Example 1

GVHD Mouse Model: Spleen Results

Figure 4A:
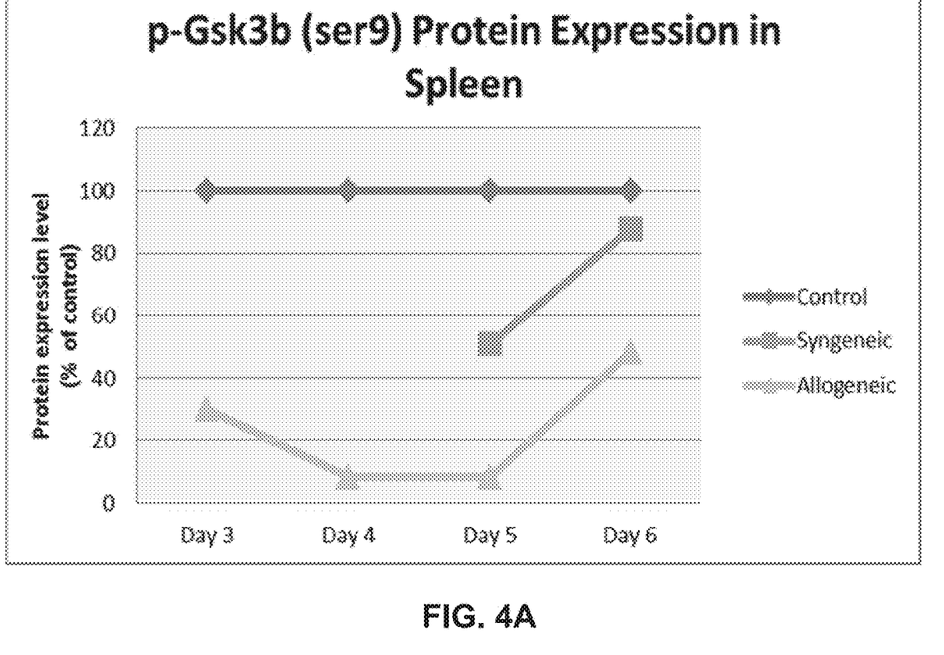
FIG. 4A is a graphical representation of ser 9-phosphorylated GSK-3β (p-GSK-3β) protein expression levels in spleen samples.
Figure 4B:
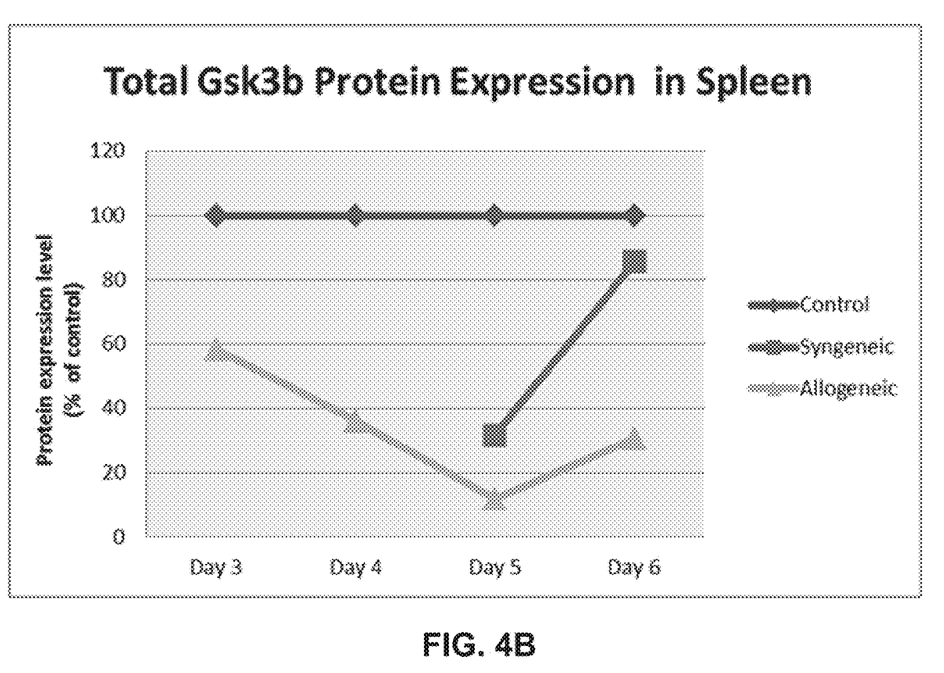
FIG. 4B is a graphical representation of total GSK-3β protein expression levels in spleen samples.

Reference is now made to FIG. 4 showing a graphical representation of the protein expression levels of p-GSK-3β (phosphorylated at ser 9 site) (FIG. 4A) and total GSK-3β (FIG. 4B) over time in spleen samples derived from Untreated (control), Syngeneic and Allogeneic mice.

The results have been normalized such that the values for the control mice were set as 100%. Each parameter was compared to the values of untreated mice.

As shown in FIG. 4, a prolonged decrease of total GSK-3β and p-GSK-3β over time was exclusively detected in the spleen of the allogeneic group mice.

It should be mentioned that in the Syngeneic group, the splenocyte population has not recovered enough to collect cells, until day 5.

In the Allogeneic group, proliferation of splenocytes was detected in the earlier days as a result of the immune response characteristic of GVHD.

On days 5 and 6, once severe symptoms have appeared in the mice, the levels of total and phosphorylated GSK-3β in the allogeneic mice were maintained at a lower level than the other groups, while in the syngeneic mice, the levels appear to approach almost normal.

Thus the results obtained show that, in the allogeneic group, p-GSK-3β and total GSK-3β decrease before the appearance of clinical symptoms (symptoms begin on day 4) and maintain lower than the untreated and Syngeneic groups throughout the disease course.

Figure 5:
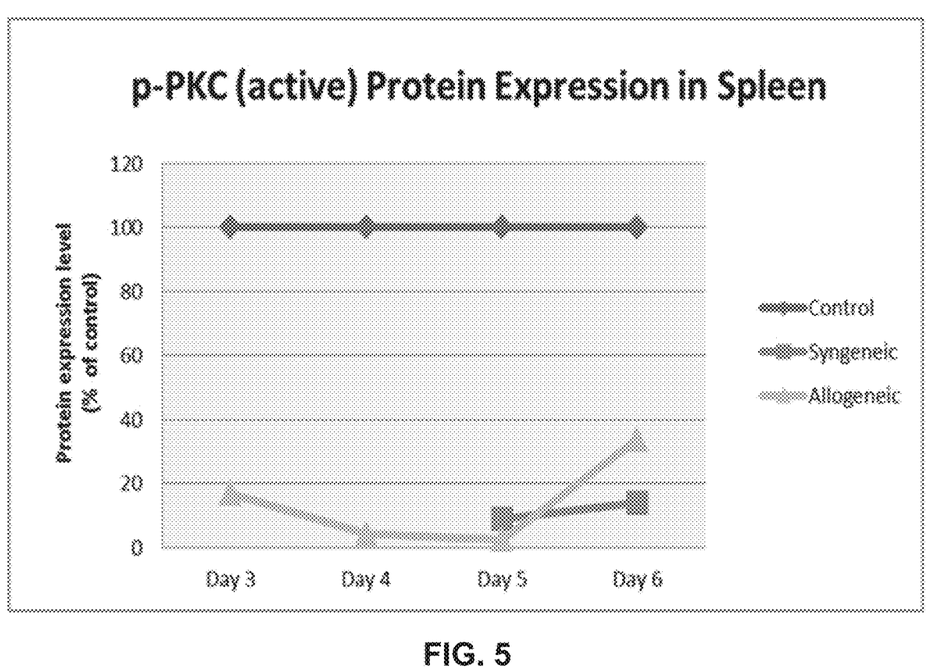
FIG. 5 is a graphical representation of phosphorylated PKC (p-PKC) protein expression levels in spleen samples.

Reference is now made to FIG. 5 showing a graphical representation of the protein expression levels of p-PKC (active form), over time in spleen samples derived from Untreated (control), Syngeneic and Allogeneic mice.

It is herein acknowledged that PKC is located upstream of GSK-3β in several pathways, and is also capable of phosphorylating GSK-3β directly.

As shown in FIG. 5, the activated PKC levels are significantly lower in splenocytes of both Syngeneic and Allogeneic mice, relative to the control.

It should be emphasised that the results obtained have been normalized such that values of the control mice were set as 100%. Each parameter was compared to the value of untreated mice independently of other parameters.

Conclusions for the Spleen Results:

The differences in the total GSK-3β and the p-GSK-3β in the spleen of the allogeneic mice compared to the syngeneic mice, can be detected as early as day 3, thus these proteins can be utilized as markers to identify and diagnose the early onset of GVHD in mice and potentially in humans.

Based on the above results, a diagnostic kit utilizing protein chip technology can be used to monitor the changes in the GSK-3β expression levels, phosphorylation levels and changes in the activation state of GSK-3β in the spleen in order to predict and detect the early onset of GVHD in humans.

Example 2

GVHD Mouse Model: Blood Results

Figure 6A:
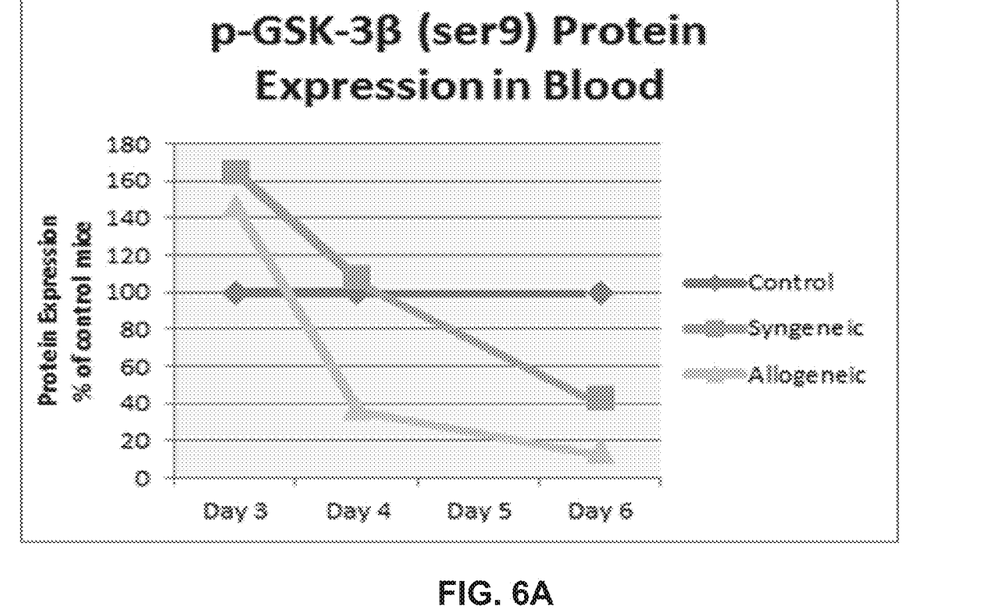
FIG. 6A is a graphical representation of ser 9-phosphorylated GSK-3β (p-GSK-3β protein expression levels in blood samples; and, FIG. 6B is a graphical representation of total GSK-3β protein expression levels in blood samples.
Figure 6B:
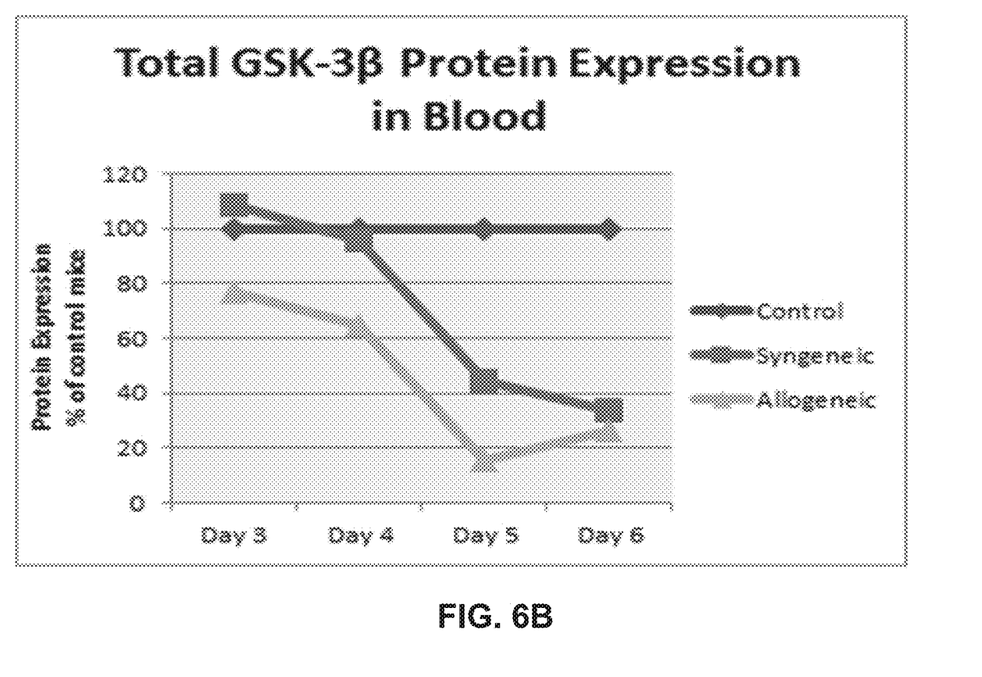

Reference is now made to FIG. 6 showing a graphical representation of the protein expression levels of p-GSK-3β (phosphorylated at ser 9 site) (FIG. 6A) and total GSK-3β

(FIG. 6B) over time in blood samples derived from Untreated (control), Syngeneic and Allogeneic mice.

As shown in FIG. 6, a prolonged decrease of total GSK-3β and p-GSK-3β in the blood was observed over time only in the allogeneic group.

In the Syngeneic group, although a decrease in total GSK-3β and p-GSK-3β is observed, it appears in a later phase than in the allogeneic mice.

In the Allogeneic group, there is a decrease in the levels of total GSK-3β and p-GSK-3β over time, which is greater than the decrease observed in the syngeneic group.

It should be mentioned that the results have been normalized such that values for the control mice were set as 100%. Each parameter was compared to the values of the untreated mice.

Conclusions for the Blood Results:

The decrease in total GSK-3β and p-GSK-3β in the blood detected in the allogeneic mice was greater than both the control and the syngeneic mice.

The decrease is most substantial on days 3 and 4, which are at the early stage of GVHD.

Based on the above results, a diagnostic kit utilizing protein chip technology can be used to monitor the changes in the GSK-3β expression levels and changes in the activation state of GSK-3β in the blood in order to predict and detect the early onset of GVHD in other mammals including humans.

Blood samples indicative of GVHD were obtained from mice, demonstrating the ability to collect usable blood samples from other mammals including humans.

Without wishing to be bound by theory, it is herein acknowledged that the detected blood levels in mice reflect that GVHD associated proliferation occurred in the spleen. Thus it can be assumed that the cells observed in the syngeneic mice on days 3, 4, and maybe 5 are cells that have existed in the periphery before the transplant. This is in contrast to the cells observed in the allogeneic mice on day 4, which are new cells that have been emerged from the spleen.

The above results demonstrate for the first time that GSK-3β is directly associated with the progression and onset of the GVHD disorder.

Example 3

Fingerprinting GVHD Disease

A further main aspect of the present invention is to explore the unique fingerprint of the GVHD disease. Such a fingerprint allows the establishment of a diagnostic kit as disclosed inter alia which comprises a set of proteins that are uniquely correlated with GVHD. In order to determine the fingerprint for GVHD, mouse model samples are analyzed by mass spectrometry to identify the following data:

The proteins that are present in the analysed system
Changes in protein expression
Changes in protein phosphorylation Based on the analysis of the mouse samples, a custom-made protein chip is prepared. The kit includes candidate molecules identified to be involved in GVHD such as antibodies against GSK-3β, the pathways and proteins associated with the regulation of the GSK-3β and the regulation of the known and established functions of the GSK-3β apoptosis markers, proliferation markers, and others (obtained by using protein analytical techniques such as western blot analysis, FACS, and fingerprinting data). The aforementioned kit is used for prognosis of GVHD and its diagnosis in early stages.

Candidate antibodies used for the GVHD protein chip include but are not limited to the antibodies recognizing the following biomarkers:

Total GSK-3β

GSK-3β ser 9 phosphorylation—indicates GSK-3β inactivation

PKC Activation—indication of GSK-3β inactivation b-catenin—inactivation of the GSK-3β through the activated Wnt Pathway Dvl—a protein upstream of GSK-3β in the Wnt pathway, and an indicator of Wnt pathway activation Akt—PI-3K signaling cascade protein which phosphorylates GSK-3β at ser 9.

Erk—Map kinase signaling cascade protein that directly phosphorylates GSK-3β at Ser9.

P38 MAPK—Map kinase signaling cascade protein that directly phosphorylates GSK-3β at Ser 389.

GSK-3β Tyrosine 216 Phosphorylation—Indicates activation of GSK-3β

Serum Albumin—has been shown to be potentially linked to GVHD onset

Markers for apoptosis (Fas, Bcl family, Cyctochrome C, caspases)

Markers for immune activity (Nf-kB, CD25)

Markers for proliferation (Cyclin D1, PCNA, p27)

In further embodiments of the invention, the protein chip results are further validated by performing a comparison with western blot data to determine the efficacy, the sensitivity, and the accuracy of the chip.

The abovementioned information is used to assess the pathways which are regulating GSK-3β in GVHD and other pathways involved in this disease.

It is a main aspect of the invention that the changes seen in the GSK-3β expression levels and activation state are herein utilized as novel markers for diagnosing the GVHD. By monitoring the changes in the GSK-3β expression levels, phosphorylation levels and changes in the activation state of the GSK-3β protein, the early onset of GVHD can be detected prior to observable clinical symptoms.

In another preferred embodiment of the invention, the use of GSK-3β as a marker allows the diagnosis of GVHD prior to the phase where observable symptoms are demonstrated by the patients and prior to the phase where the host body is attacked by the T-cells.

In further embodiments of the invention, Western blot analysis of mouse splenocyte lysates is performed using at least one of the following proteins as potential markers for GVHD:

b-catenin—a marker for the inactivation of the GSK-3β through the activated Wnt Pathway.

Dvl—a protein upstream of GSK-3β in the Wnt pathway, and an indicator of Wnt pathway activation.

Akt—PI-3K signaling cascade protein which phosphorylates GSK-3β at ser 9.

Erk—Map kinase signaling cascade protein that directly phosphorylates GSK-3β at Ser 9.

P38 MAPK—Map kinase signaling cascade protein that directly phosphorylates GSK-3β at Ser 389.

GSK-3β tyr 216 phosphorylation—Indicates the activation of the GSK-3β.

In further embodiments of the invention, Western blot analysis of mouse blood lysates is performed using GSK-3β, p-GSK-3β, PKC, and at least one of the antibodies listed above as potential markers for GVHD.

In a further embodiment of the invention, livers from GVHD model mice are used to perform analysis of GSK-3β and related proteins using western blot and/or mass spectrometry techniques or any other technique used for protein analysis.

It is also within the scope of the present invention that the regulation of GSK-3β expression is tested in a time-course study of an acute GVHD mouse model. Thus by GSK-3β manipulation GVHD onset can be prevented.

In a further embodiment of the invention, the substrates of the GSK-3β and the products associated with said substrates are identified.

In a further embodiment of the invention, the aforementioned substrates and products which are specific for the GVHD disorder are found. Those substrates and products are used for increasing the sensitivity of the diagnostic technology provided by the present invention.

In a further embodiment of the invention the specific pathway that stimulates the specific change in the activation state of the GSK-3β associated with the specific disorder of interest such as GVHD is identified. Such candidates that stimulate the activation state of the GSK-3β may include:

Dsh—Wnt pathway (upstream of GSK-3β)
  Associated with inactivation of the GSK-3β through the activated Wnt pathway
Akt—PI-3K/Akt pathway
  Associated with Ser 9 inactivation of the Wnt pathway
cAMP—Associated with Ser 9 inactivation of the GSK-3β

The above described information indicates the pathways that are regulating the activation state of the GSK-3β in the specific disorder of interest such as GVHD. These results are used for fingerprinting a specific disease associated with activation state of the GSK-3β. Such fingerprinting data is used to increase the sensitivity of the diagnostic kit for the disease of interest.

Example 4

Clinical Study Using the GVHD Diagnostic Kit

The following clinical study is conducted in association with a CRA (clinical research associate), including Helsinki approval and negotiations with medical centers:

Patients for the clinical trial are recruited (including Helsinki approval and negotiations with medical centers).

Blood samples are collected from the patients who have undergone bone marrow transplants (throughout the year).

Protein chip or any other protein analytical technique is utilized for analysis of the human samples to test its efficacy in predicting acute GVHD onset. This is a retrospective study. The kit analysis results are compared against the diagnostic outcome (according to current medical standards) for each patient.

If necessary, the kit is calibrated by assaying human samples using western blot analysis.

Reference is now made to a research protocol describing early diagnosis of Graft-Versus-Host-Disease (GVHD) by utilizing specific molecular biomarkers in patient who undergo hematopoietic stem cell transplantation (HSTC).
Research Aims:
  Determining the aGVHD (acute Graft-versus host disease) molecular pattern in human patients.
  Testing the efficacy and accuracy of the GVHD Diagnostic Kit in diagnosing aGVHD.
Rationale:
  Based on the function of GSK-3β in T-cell proliferation it can be utilized as a diagnostic tool for the detection of GVHD. The results in mice shown above demonstrate that two of the components of the diagnostic technology of the present invention, the activation state of the GSK-3β and the substrates of the GSK-3β and their particular products, play a central role in the onset and progress of GVHD, and can be utilized as a diagnostic kit for the early detection of GVHD. Based on the results in mice shown by the current invention, a proof of concept study in human is presented below.
Research Protocol:
  Monitoring the expression/phosphorylation levels of biomarkers in the GSK3β pathway which predict the onset and progression of GVHD.
  Detecting the expression/phosphorylation levels of biomarkers in the GSK3β pathway in white-blood-cells from the donor of the stem cells, before and after G-CSF (Granulocyte-colony stimulating factor) (neupogen or other) stimulation.
  Monitoring the expression/phosphorylation levels of biomarkers in the GSK3β pathway in white-blood-cells from the recipient before and up to 100 days after transplantation (blood sampling times are indicated below).
  Analyzing the data (covariate/multi-variate) and identifying a pattern of expression/phosphorylation levels of the different biomarkers in the GSK3β pathway in patients who developed aGVHD versus patients who did not develop aGVHD.
Methods:
Phase 0 Healthy Volunteers:
  Healthy volunteers consist of men and women between the ages 20 to 80.
Procedure:
  Volunteers are recruited. Healthy volunteers are asked to give a blood sample (5 ml in anti-coagulant tube) for calibrating the system. This phase should include about 10 volunteers. Volunteers should sign an informed consent.

The blood samples are processed with Erythrocyte lysis buffer.

Part of the samples is stimulated in vitro using different conditions (e.g. anti-CD3, mitogens).

Part of the samples is counted for the number of white-blood-cells, in order to calibrate the sensitivity of the process.

Initial Processing of the blood samples: The blood is centrifuged, subjected to erythrocyte lysis buffer (removal of red blood cells) and washed. Cells are then subjected to a whole cell lysis buffer and lysates are stored at −80° C. Same is done to cells after stimulations (stage 3 above).

Secondary Processing of the samples: Samples collected, are processed with the GVHD protein chip of the present invention by the following steps:
  Taking the samples from −80° C.
  Incubating a sample of each lysate on a different array on the protein chip.
  Washing the protein chips.
  Incubating the protein chip with secondary antibodies.
  Washing the protein chips.
  Reading the protein chips.
  Mass-spectrometry: Some samples are sent for mass-spectrometry analysis after immuno-precipitation with GSK3β antibody.
  Learning the sensitivity and the expression/phosphorylation pattern of the antibodies (according to the targeted proteins) in the different conditions.
Phase I Donors and Patients:
  The patients who participate in this trial are patients who undergo bone marrow transplantation in the department of Bone-marrow Transplantation. It involves men and women between the ages 20 to 80 who have to undergo bone-marrow transplantation. The background to the transplant can vary from bone marrow failure due to severe aplastic anaemia, Leukaemia, non-Hodgkin's lymphoma, certain genetic blood and immune system disorders such as sickle cell anemia, thalassemia and some severe immune system diseases.

The expression/phosphorylation levels of the different biomarkers in the GSK3β pathway in patients who developed aGVHD is assessed and compared to patients who did not develop aGVHD.

Biochemistry:

Information obtained from the routine clinical and laboratory checkups of the patients is obtained. This information should assist in assessing the condition of the patient and learning about confounders for GVHD.

GVHD Pattern Analysis:

To determine the pattern of expression of the biomarkers in the development of aGVHD, the expression/phosphorylation levels of the different biomarkers in the GSK3β pathway is analyzed (over-time) in patients who developed aGVHD versus patients who did not develop aGVHD.

Biomarkers in the GSK3β Pathway:

This trial is focused on major components of the GSK3β pathway that are most probably playing a role in aGVHD. The expression/phosphorylation levels of these components are checked by a protein chip (or other protein analytical techniques such as Westerns or ELISA if necessary).

Mass-Spectrometry:

Some samples are sent for mass-spectrometry analysis, in order to identify the sites on the GSK3β that are phosphorylated in aGVHD patients and are not phosphorylated in patients who didn't develop aGVHD. This information is utilized in distinguishing the GVHD pattern and for a better understanding of the pathways that are involved in the onset and progression of aGVHD.

Flow Cytometry:

Some samples are sent for flow-cytometry analysis, in order to identify the subgroups of cells that are involved in GVHD. This information is utilized for a better understanding of the cells and pathways that are involved in the onset and progression of aGVHD.

Procedure:

Recruiting the donors. Donors who arrive to donate hematopoietic stem cells are asked to participate in the trial. The donors sign an informed consent.

Collecting Blood from the donors. Every donor is having a series of blood tests to assess his condition. Another 5 ml is taken before and after G-CSF stimulation. Immediately after collecting the blood, it is processed and stored at −80° C. The blood is centrifuged, subjected to erythrocyte lysis buffer (removal of red blood cells) and washed. Cells are then subjected to a whole cell lysis buffer and lysates are stored at −80° C.

Recruiting the patients and signing them on informed consent. About 30 patients are recruited who undergo HSCT transplantation. According to the clinical statistics, about 7-10 patients are expected to develop aGVHD. Since it isn't know who will develop aGVHD, all the 30 patients are monitored. The samples from patients that didn't develop GVHD are used as controls.

Getting the information from the routine biochemical tests. The patients undergo frequent routine tests for components in their blood and urine including blood counts and tests for contamination.

Monitoring the patient: Every patient is having a series of blood tests to assess his condition before and after the transplantation. Another 5 ml is taken in each of the following 28 time points, on the following days post-transplant: (−)10, 1, 2, 4, 6, 8, 10, 12, 14, 17, 20, 23, 26, 29, 33, 37, 41, 46, 51, 56, 62, 68, 74, 81, 88, 96, 102 and 110 days.

Flow-cytometry: Some of the blood samples are taken for flow-cytometry analysis. In this analysis the cells subgroups (e.g. CD4+ vs. CD8+ cells) are monitored.

Initial processing of the blood samples: The processing of the sample needs to be started within 30 minutes after collecting the blood. Once the process is completed samples can be stored at −80° C. The blood is centrifuged, subjected to erythrocyte lysis buffer (removal of red blood cells) and washed. Cells are then subjected to a whole cell lysis buffer and lysates are stored at −80° C.

Secondary processing of the samples: After collecting enough samples, they are processed with the GVHD protein chip of the present invention by the following steps:

Taking the samples from −80° C.

Incubating a sample of each lysate on a different array on the protein chip.

Washing the protein chips.

Incubating the protein chip with secondary antibodies.

Washing the protein chips.

Reading the protein chips.

It is noted that other standard protein analytical techniques such as Westerns or ELISA can be utilized if necessary.

Mass-spectrometry: Some samples are sent for mass-spectrometry analysis, after immuno-precipitation with GSK3β antibody.

Comparing the expression/phosphorylation pattern of the antibodies (according to the targeted proteins) to the clinical status and aGVHD diagnosis.

Once the patient is diagnosed with GVHD, or early onset of aGVHD, a proper treatment should be initiated by the physician.

Some management and treatment protocols are as follow (http://emedicine.medscape.com/article/429037-overview, incorporated hereinafter by reference):

The criterion standard for primary prophylaxis of acute GVHD is cyclosporin A for 6 months and short-course methotrexate in T-cell-replete allogeneic HCT (criterion standard); tacrolimus is often substituted for cyclosporine, especially in unrelated-donor transplantation. Prednisone may be added. Antithymocyte globulin (ATG) can be given before HCT.

Primary therapy for acute GVHD may be as follows:

For skin GVHD of stage I or II, observation or a trial of topical corticosteroids (e.g. triamcinolone 0.1%) may be used.

For grade II-IV acute GVHD, continuing the original immunosuppressive prophylaxis and adding methylprednisolone (1-60 mg/kg, most commonly starting at 2 mg/kg/day in 2 divided doses); in patients who respond to initial therapy, short-term tapering treatment with prednisone to a cumulative dose of 2000 mg/m$^2$ Other therapies are antithymocyte globulin (ATG), cyclosporine alone, mycophenolate mofetil (MMF), daclizumab, anti-IL-2 receptor, anti-CD5-specific immunotoxin, and a pan T-cell ricin A-chain immunotoxin (XomaZyme), alone or in combination.

Secondary therapy for acute GVHD is as follows:

ATG or multiple pulses of methylprednisolone (at doses higher than those used in initial therapy)

MMF at 2 g daily, added to the steroid regimen

Muromomab-CD3 (Orthoclone OKT3)

Humanized anti-Tac antibody to the IL-2 receptor

Psoralen and ultraviolet A irradiation (PUVA), for cutaneous lesions

Tacrolimus, for GVHD with cyclosporine resistance or neurotoxicity

Therefore, it is within the scope of the present invention to enable treatment to a patient (i.e. by a physician) after being diagnosed for GVHD, early onset of GVHD, acute GVHD, said treatment being an effective amount of immunosuppressant, steroids or any other pharmaceutical agent effective in treatment of GVHD.

What is claimed is:

1. A diagnostic kit for detecting Graft versus host disease (GVHD) in a mammalian subject undergoing a transplant, before the appearance of clinical symptoms, said kit comprising a bound antibody-based protein chip, for identifying and quantifying changes in at least one parameter selected from the group consisting of:
   a. expression levels of a biomarker selected from a group consisting of: total glycogen synthase kinase-3β (GSK-3(3), serine 9 phosphorylated GSK-3β (p-GSK-3β ser 9), tyrosine 216 phosphorylated GSK-3β (p-GSK-3β tyr 216), β-catenin, protein kinase C (PKC), and any combination thereof; and
   b. phosphorylation levels of a biomarker selected from a group consisting of: total glycogen synthase kinase-3β (GSK-3β), serine 9 phosphorylated GSK-3β (p-GSK-3β ser 9), tyrosine 216 phosphorylated GSK-3β (p-GSK-3β tyr 216), β-catenin, protein kinase C (PKC), and any combination thereof;
   wherein, said changes in said parameters are compared to predetermined control values obtained from healthy subjects, patients of syngeneic transplants and/or measurements taken from said mammal prior to transplant, further wherein said changes show at least one of the following results:
      i. at least about 25% deviation in said expression levels or phosphorylation levels of total GSK-3β;
      ii. at least about 25% deviation in said expression levels or phosphorylation levels of p-GSK-3β ser 9;
      iii. at least about 25% deviation in said expression levels or phosphorylation levels of p-GSK-3β tyr 216;
      iv. at least about 25% deviation in said expression levels or phosphorylation levels of phosphorylated PKC;
      v. at least about 25% deviation in said expression levels or phosphorylation levels of β-catenin; or
      vi. any combination thereof;
   wherein, said deviation percentage in said parameters is obtained by comparing parameter values obtained from subjects after transplant to parameter values obtained from subjects prior to transplant,
   wherein, said bound antibody-based protein chip comprises an array of bound antibodies against biomarkers and/or antigens for determining said expression levels, phosphorylation levels or a combination thereof of said total GSK-3β, p-GSK-3β ser 9, p-GSK-3β tyr 216, PKC and β-catenin,
   wherein, said bound antibody-based protein chip further comprises antibodies against antigens and/or biomarkers for detecting apoptosis, proliferation or other biological and biochemical processes relevant to GVHD selected from the group consisting of: Dvl, Akt, Erk, P38 MAPK, Serum Albumin, markers for apoptosis comprising Fas, Bcl family, Cytochrome C and caspases, markers for immune activity comprising Nf-kB and CD25, markers for proliferation comprising Cyclin D1, PCNA and p27, and any combination thereof, and
   wherein, said bound antibody-based protein chip comprises said array of antibodies bound to a glass slide or equivalent substrate, thereby providing a protein chip analysis tool.

2. The diagnostic kit of claim 1, wherein said kit is designed for monitoring the progression of said GVHD in said mammalian subject.

3. The diagnostic kit of claim 1, wherein at least one of the following holds true: (a) said kit is designed for the detection and quantification of the activation/inactivation status of GSK-3β, (b) said activation/inactivation status of GSK-3β is an indicator of the cause of GVHD.

4. The diagnostic kit of claim 1, wherein said kit is used for GVHD detection in a tissue sample obtained from said mammalian subject, selected from a group consisting of: blood, spleen, liver, skin, lungs, gastrointestinal tract and any combination thereof.

5. The diagnostic kit of claim 1, wherein said kit is designed for detecting GVHD at phase II of said disease, prior to the appearance of clinical symptoms.

* * * * *

UNITED STATES PATENT AND TRADEMARK OFFICE
CERTIFICATE OF CORRECTION

PATENT NO. : 11,747,337 B2
APPLICATION NO. : 16/694379
DATED : September 5, 2023
INVENTOR(S) : Stephen G. Marx It is certified that error appears in the above-identified patent and that said Letters Patent is hereby corrected as shown below:

In the Claims

Column 23, Lines 19-20, Claim 1, delete "(GSK-3(3))," and insert -- (GSK-3β), --

Signed and Sealed this
Twenty-first Day of November, 2023

Katherine Kelly Vidal
Director of the United States Patent and Trademark Office